United States Patent
Slosek et al.

[11] 4,067,069
[45] Jan. 10, 1978

[54] SAFETY GOGGLE

[75] Inventors: Patrick F. Slosek, Dudley, Mass.; Robert R. Fischlein, Woodstock, Conn.

[73] Assignee: American Optical Corporation, Southbridge, Mass.

[21] Appl. No.: 697,907

[22] Filed: June 21, 1976

[51] Int. Cl.² ............................................. A61F 9/02
[52] U.S. Cl. ..................................................... 2/441
[58] Field of Search .................. 2/441, 439, 440, 443, 2/444, 436

[56] References Cited
U.S. PATENT DOCUMENTS

| | | | |
|---|---|---|---|
| 1,565,890 | 12/1925 | Baker | 2/441 |
| 1,722,602 | 7/1929 | Tillyer et al. | 2/437 |
| 3,267,488 | 8/1966 | Colvin | 2/440 |
| 3,363,262 | 1/1968 | Lindblom | 2/441 |

FOREIGN PATENT DOCUMENTS

| | | | |
|---|---|---|---|
| 289,074 | 2/1969 | Australia | 2/441 |
| 1,214,206 | 11/1959 | France | 2/441 |

*Primary Examiner*—Werner H. Schroeder
*Assistant Examiner*—Peter Nerbun
*Attorney, Agent, or Firm*—Howard R. Berkenstock, Jr.

[57] ABSTRACT

A goggle for protection against dust and impact damage to the eyes including a pliable, contoured facemask having a pair of forwardly extending cage portions each adapted to receive and fixedly support a rigid eyecup. Each eyecup, in turn, supports an impact and shatter-resistant safety lens held in place with a resilient O-ring. Sides of the eyecup are provided with openings covered with dust-filtering and impact-resistant double screening. The eyecups are readily manually insertable into and removable from cage portions of the pliable facemask and each, in turn, is adapted to selectively internally support an adapter for an auxiliary ophthalmic prescription lens.

5 Claims, 7 Drawing Figures

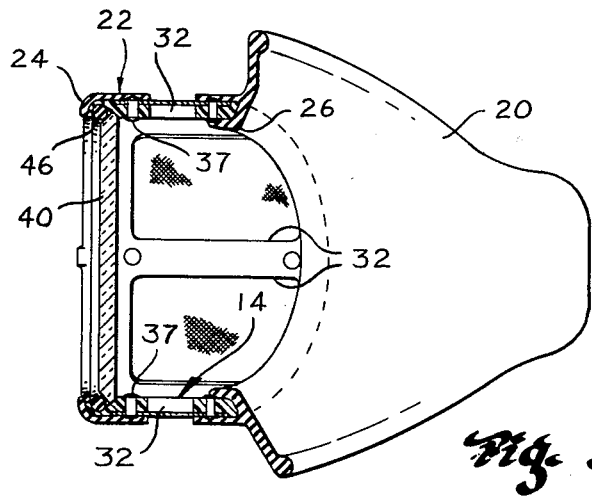
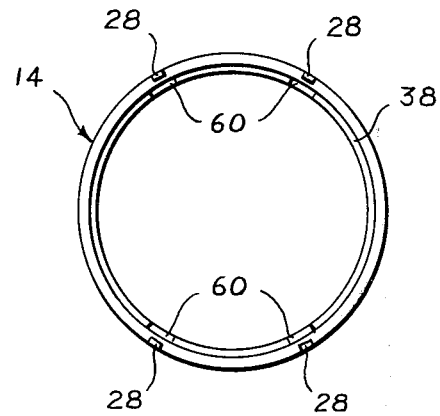
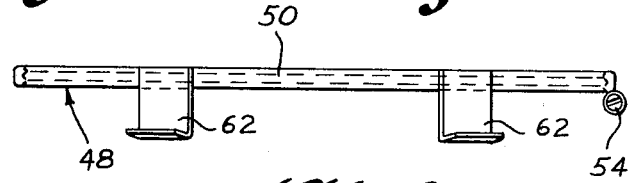
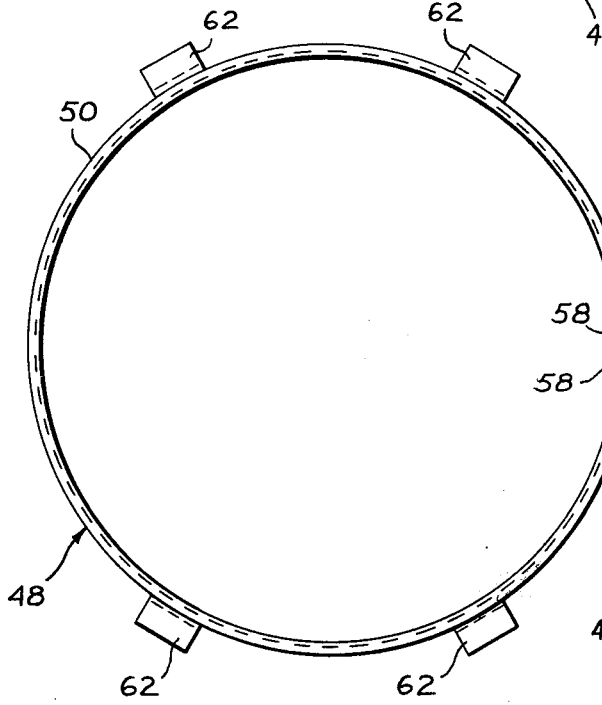
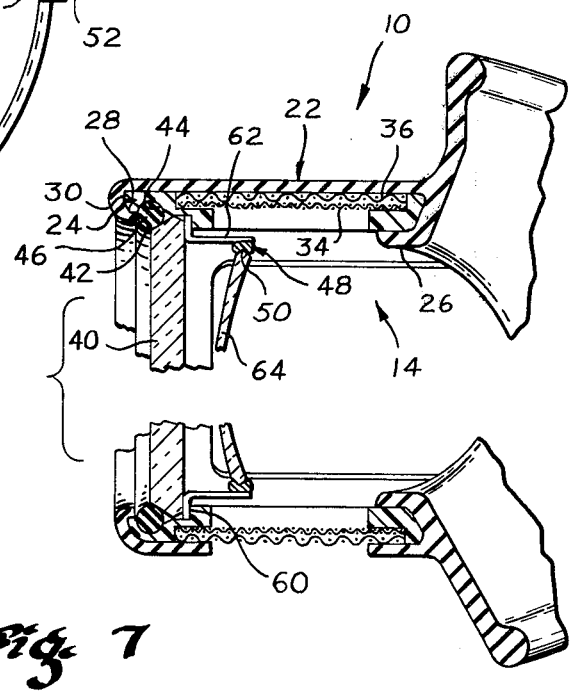

4,067,069

SAFETY GOGGLE

BACKGROUND OF THE INVENTION

1. Field of the Invention

This invention relates to improvements in safety goggles and has particular reference to goggles of the dual eyecup type for protection against injury from particle impact and ambient dust.

2. Discussion of the Prior Art

In cases where protection against foreign object impact and/or dust is required, it is customary to utilize a ventilated dual eyecup goggle having a relatively large facemask. With such means, readily replaceable individual lenses of exceptionally high resistance to impact damage can be provided and the large area of facial contact about the eyecups affords the opportunity to minimize leakage of ambient dust into the cups.

Heretofore, however, facemasks have been cut from flat stock and sewn into shapes deemed best for fitting about the eyes. The sewing usually includes the addition of marginal bindings and/or linings of material preselected to afford gentle contact with the face; and goggle eyecups being separately stitched, stapled, cemented or riveted to the facepiece.

These awkward and time-consuming operations and need for special manufacturing equipment has rendered the cost of the goggles excessive and, in end product result, lacking in wearing comfort and effectiveness against dust.

Excessive weight and ungainliness as well as the high cost resulting in large part from complexity of structure and tediousness of current goggle-manufacturing procedures indicate a serious need for improvements in both product design and processing.

It is, accordingly, an object of the present invention to simplify the goggle structure, its manufacturing procedure and to reduce cost, all with the benefit of superior product quality and effectiveness.

Other objects and advantages will become apparent from the following description of the invention.

SUMMARY OF THE INVENTION

The object of the invention and its corollaries are accomplished by provision of a one-piece molded pliable facemask having a face-engaging section contoured to the general configuration of portions of the face surrounding the two orbits. Extending forwardly and integral with the face-engaging section of the mask are a pair of cage portions each adapted to internally receive and fixedly but detachably support a rigid eyecup.

Each eyecup is forwardly grooved to receive and support an impact and shatter-resistant safety lens which is held and sealed in place with a resilient O-ring. Sides of the eyecups are provided with ventilation openings which are covered with dust-filtering and impact-resistant double screens. An inwardly disposed screen having a fineness of mesh capable of preventing passage of dust particles is protected by an outer covering of relatively heavy gage open mesh impact-resistant screening.

The eyecups are readily manually insertable into and removable from cage portions of the pliable facemask and each, in turn, is constructed and arranged to support an adapter for an auxiliary prescription lens.

Details of the invention will become apparent from the following description when taken in conjunction with the accompanying drawings.

IN THE DRAWINGS

FIG. 3 is a vertical cross-sectional view taken along line 3—3 of FIG. 1;

FIG. 4 is a front elevational view of one eyecup component of the goggle structure, the eyecup lens and lens retainer having been removed for clarity in illustrating underlying features thereof;

FIG. 5 is a front elevational view of auxiliary lenssupporting means which is adaptable to the goggle structure of FIGS. 1-4;

FIG. 6 is a top plan view of the auxiliary lensholding means; and

FIG. 7 is an enlarged cross-sectional view taken along line 7—7 and illustrating use of the auxiliary lenssupporting means according to the invention.

DESCRIPTION OF THE PREFERRED EMBODIMENTS

With reference to the drawings, it can be seen that safety goggle 10 comprises the three basic elements of a facepiece 12, a pair of eyecups 14 and a headband 16 for holding the goggle structure in place during use.

Facepiece 12 is formed of a soft, non-irritating but durable material such as, for example, a non-toxic polyvinyl chloride molded as a one-piece unit.

Figure 1:
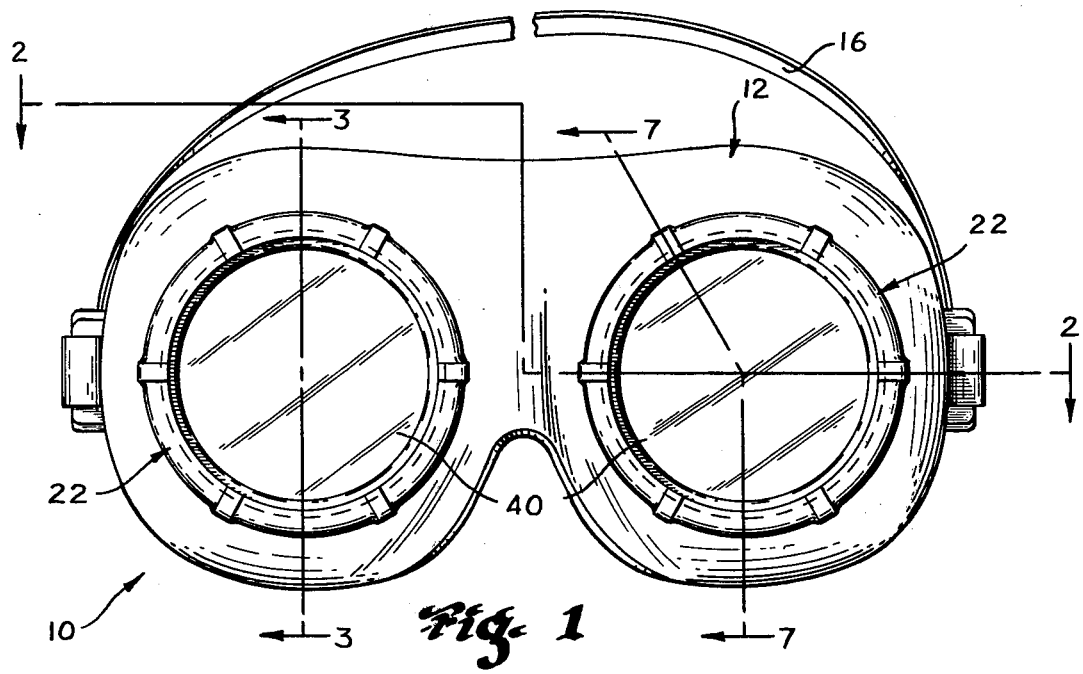
FIG. 1 is an illustration, in front elevation, of a preferred embodiment of the invention.
Figure 2:
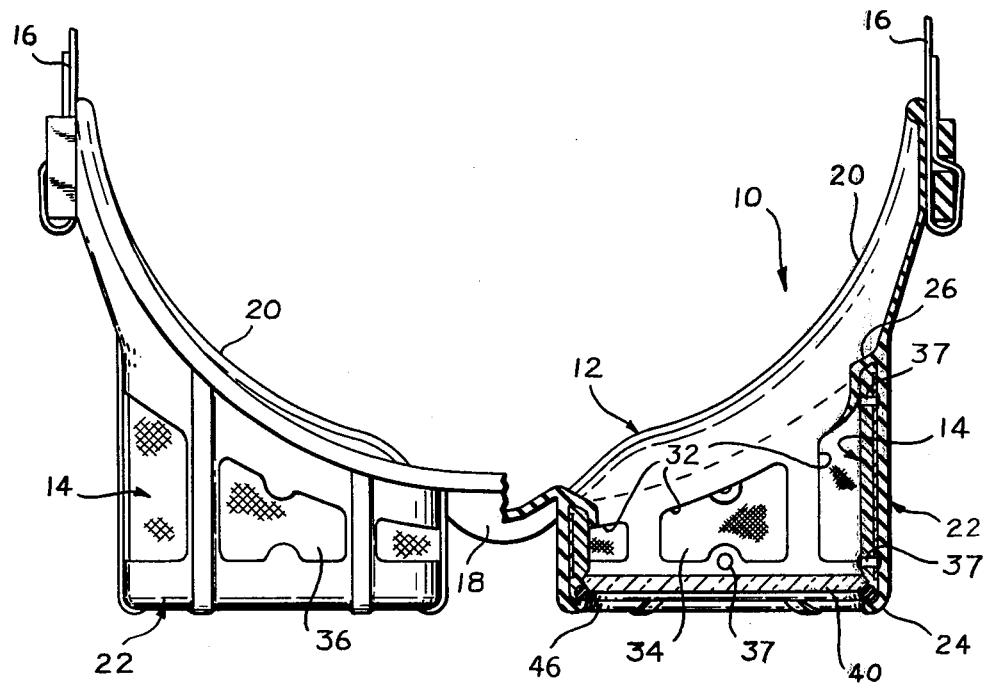
FIG. 2 is a partially cross-sectioned view of the safety goggle of FIG. 1 taken generally along line 2—2.

The molded unit includes a facemask portion 18 having a rearwardly disposed face-engaging margin 20 (FIGS. 2 and 3) shaped to extend about the facial orbits, across the forehead and over the nose in a comfortable but tight-sealing relationship with the skin. The facemask, being soft and pliable as mentioned above, is readily conformable to all facial contours thus rendering the goggle universal in fitting.

Integral with and extending forwardly of the facemask portion 18 is a pair of open cage portions 22 into each of which is detachably fitted one of eyecups 14. Cage portions 22 are provided with forwardly and rearwardly disposed lips 24 and 26 respectively which may be elastically deformed to receive the forward and rearward edges of eyecups 14 and thereafter return to their initially molded configuration to fix the cups in place.

The forward edge of each of cups 14 is provided with a plurality of key-like protrusions 28 (FIGS. 4 and 7) which become engaged in receiving recesses 30, one of which can be seen in FIG. 7, for establishing and fixing the rotational orientation of cups 14 in their respective cages 22. Eyecups 14 are formed of a rigid cast or molded plastic material such as, for example, an acetal copolymer. Other rigid plastic materials known and commonly used in the trade may, of course, be employed to form eyecups 14. The eyecups are of a generally tubular configuration each having an open lens-receiving forward end and an opposite sloping end adapted to fit beneath lip 26 of facepiece 12. Sides of the eyecups are provided with ventilating openings 32 over which a dual dust and impact-resistant screening system is placed.

The system of screens comprises an inner closely woven (e.g. 150 mesh) stainless steel screen 34 (FIGS. 2 and 7) over which is provided a heavier, more open mesh (e.g. 16 mesh) impact-resistant screen 36. Rivets 37 are illustrated as being used to hold the dual screen construction in place. Other fastening means, including staples and cements may, however, be used to suit particular requirements.

Referring more particularly to FIG. 7, it will be noted that each eyecup 14 is provided with a lens-receiving seat 38 against which a conventional shatter-resistant safety lens 40 is removably and replaceably seated. Such lenses are conventionally formed of tempered or chemcially-treated glass and are each provided with a forwardly directed peripheral bevel 42. Each eyecup 14 is provided with a marginal groove 44 preferably of a semi-circular cross-sectional shape into which O-ring 46 is inserted against bevel 42 for fixing lens 40 in place.

O-ring 46, being readily removable and reusable, affords economical and highly efficient retaining means permitting simple and rapid on-the-spot replacement of damaged lenses 40. The O-ring is preferably formed of neoprene or a similar material which is impervious to most atmospheric conditions and has a useful life span corresponding to that of facepiece 12 thereby minimizing goggle replacement parts to damaged safety lenses 40 only.

From the foregoing, it can be seen that manufacturing operations are minimized. They comprise only the molding of facepiece 12 and eyecups 14 to shape, the cutting of screens 34 and 36 to size and shape and fastening the screens to the eyecups.

Assembly of the goggle involves only a simple hand operation of inserting each eyecup 14 into a respective one of cage portions 22 of facepiece 12. Tools are not required.

Prior art facepiece lining, binding, stitching and eyecup fastening operations have all been obviated by the present invention.

In FIGS. 5 and 6, there is illustrated an adapter 48 into which a lens incorporating a person's ophthalmic prescriptive correction may be mounted.

Adapter 48 comprises lens rim 50 which is split at lime 52 (FIG. 5) and clamped together by screw 54 extending through lugs 56 and 58, one attached to each of opposite ends of the split rim 50.

When needed by the intended wearer of goggle 10, his right and left eye ophthalmic prescription lenses, each mounted in one of adapters 48, are placed in right and left eye eyecups respectively of the goggle behind safety lens 40 in each case.

Referring more particularly to FIGS. 4 and 7, it can be seen that recesses 60 are provided in lens seat 38 of each eyecup 14 into which terminal portions of L-shaped clips 62 of adapters 48 are placed as shown in FIG. 7. Lens 40 is positioned against seat 38 hold adapter 48 in place and O-ring 46 completes the assembly.

By such means a prospective goggle wearer's prescription ophthalmic lens, one of which is illustrated as lens 64 in FIG. 7, may be readily yet removably positioned for use. The ophthalmic prescription lens 64 is located rearwardly of safety lens 40 within cup 14 and thus is protected from damage due to abrasion, splash or particle impact occurring ambiently of goggle 10.

While only four recesses 60 are illustrated in FIG. 4, it is contemplated that more may be provided to permit various other rotational orientations of adapters 48, with prescription lenses, in the eyecups. Normally, however, axes of astigmatism of the prescription lenses would be preset relative to locations of clips 62 on rims 50.

Those skilled in the art will readily appreciate that there are various modifications and adaptations of the precise form of the invention here shown which may suit particular requirements. Accordingly, the foregoing illustrations are not to be interpreted as restrictive beyond the extent necessitated by the following claims.

We claim:
1. a goggle comprising:
   a one-piece pliable facepiece of soft non-toxic material having an elastic memory, said facepiece further having a rearwardly-disposed continuous face-engaging margin adapted to extend without interruption across the brow about the temples and over the nose and cheeks of a wearer and a pair of forwardly-extending generally cylindrical eyecup cage portions each having an eyecup retaining lip adaptable to deformation for receiving an eyecup and returnable to its initially-molded configuration for fixing the eyecup in place, each of said cage portions further having a series of lateral openings;
   a rigid lens-supporting eyecup in each cage portion, said eyecups being of a tubular configuration and having side openings positionally matching said lateral openings in respective cage portions, said side openings in said eyecups each being screened with a first inwardly-disposed fine mesh screen for preventing passage of fine particulate matter and a second outer relatively coarse mesh screen for resisting damage to said first screen by large particle impact and each of said eyecups still further having a forwardly-directed lens-receiving seat;
   a safety lens disposed against said seat in each eyecup; and
   means for retaining said lenses so in place.

2. A goggle comprising:
   a one-piece pliable facepiece having a rearwardly-disposed continuous face-engaging margin adapted to extend without interruption across the brow, above the temples and over the nose and cheeks of a wearer and a pair of forwardly-extending laterally apertured eyecup cage portions;
   a pair of rigid lens-supporting eyecups, one fitted internally of each of said cage potions, said eyecups each having a forwardly-directed lens-receiving seat;
   a safety lens disposed against said seat in each eyecup;
   means for retaining said lenses so in place; and
   an ophthalmic prescription lens-supporting member in each of said eyecups, said lens-supporting member comprising a rim into which said prescription lens may be clamped and attachment clips secured to said rim.

3. A goggle according to claim 2 wherein said rim is split at one point in its extension, connecting lugs are affixed thereto one adjacent each side of said split and said lugs are detachably connected together.

4. A goggle according to claim 2 wherein said safety lens-receiving seat in each of said eyecups is provided with spaced recesses, a terminal portion of each of said clips of said prescription lens-supporting member is fitted into one of said recesses, said safety lens being positioned over said ends of said clips when placed against said seat whereby said prescription lens-supporting member is held in place and said detachable safety lens-retaining means completes the assembly of lenses and eyecup.

5. A goggle comprising:

a one-piece pliable facepiece having a rearwardly-disposed continuous face-engaging margin adapted to extend without interruption across the brow, about the temples and over the nose and cheeks of a wearer and a pair of forwardly-extending laterally-apertured eyecup cage portions each having an eyecup-retaining lip adaptable to deformation for receiving an eyecup and returnable to its initially-molded configuration for fixing the eyecup in place;

a pair of rigid lens-supporting eyecups, one fitted internally of each of said cage portions of said facepiece, said eyecups each having a forwardly-directed lens-receiving seat;

a safety lens disposed against said seat in each eyecup; and a resilient O-ring retaining each of said lenses so in place.

* * * * *